United States Patent [19]
Gnad et al.

[11] 3,979,378
[45] Sept. 7, 1976

[54] WATER-SOLUBLE AZO DYES HAVING A SUBSTITUTED 2-HYDROXYPYRIDONE (6) COUPLING COMPONENT

[75] Inventors: Gerhard Gnad; Günther Lamm; Johannes Dehnert, all of Ludwigshafen, Germany

[73] Assignee: Badische Anilin- & Soda-Fabrik Aktiengesellschaft, Ludwigshafen (Rhine), Germany

[22] Filed: Jan. 27, 1971

[21] Appl. No.: 110,249

[30] Foreign Application Priority Data
Jan. 31, 1970 Germany............................ 2004487

[52] U.S. Cl. ................................................ 260/156
[51] Int. Cl.² ...................... C09B 29/36; D06P 3/24
[58] Field of Search ..................................... 260/156

[56] References Cited
UNITED STATES PATENTS

| 3,619,112 | 11/1971 | Berrie .................................. 260/156 |
| 3,640,674 | 2/1972 | Berrie et al. ..................... 260/156 X |
| 3,664,996 | 5/1972 | Berrie et al. ......................... 260/156 |

Primary Examiner—Floyd D. Higel
Attorney, Agent, or Firm—Johnston, Keil, Thompson & Shurtleff

[57] ABSTRACT

Azo dyes containing sulfonic or carboxylic acid groups and having a substituted 2-hydroxypyridone-(6) as coupling component. The dyes are particularly valuable for dyeing natural or synthetic polyamides.

2 Claims, No Drawings

WATER-SOLUBLE AZO DYES HAVING A SUBSTITUTED 2-HYDROXYPYRIDONE (6) COUPLING COMPONENT

The invention relates to azo dyes having the general formula (I):

$$\left(D-\left[-N=N-\underset{HO}{\underset{N}{\bigcirc}}\overset{A^1}{\underset{R}{\bigcirc}}\overset{A^2}{=}O\right]_m\right)(X)_n \quad (I)$$

where

D denotes the radical of an aromatic diazo or tetrazo component;

R denotes hydrogen or unsubstituted or substituted alkyl, cycloalkyl, aralkyl or aryl having a total of one to eight carbon atoms;

$A^1$ denotes methyl, ethyl, propyl, butyl or phenyl;

$A^2$ denotes cyano, carbamoyl or carbalkoxy;

X denotes a sulfonic acid or carboxylic group or a radical having the formula $-SO_2-NH-SO_2-Y$;

Y denotes alkyl, aryl or unsubstituted or substituted carbamoyl;

$m$ denotes one of the integers 1 and 2; and $n$ denotes one of the integers 1, 2 and 3.

The groups X may be situated in the radical D or in the radical R when R denotes aryl, or in both.

Examples of specific radicals R are (besides hydrogen) alkyl radicals having one to eight carbon atoms such as methyl, butyl, hexyl or β-ethylhexyl, cyclohexyl, benzyl, phenylethyl and phenyl bearing chlorine; bromine, methyl, ethyl, methoxy, ethoxy and/or sulfonic acid as a substituent. The alkyl groups in particular may bear hydroxy groups or alkoxy groups as substituents or may have oxygen atoms in the chain as in the case of polyglycol ethers.

Examples of carbalkoxy groups $A^2$ are carbethoxy, carbopropoxy, carbobutoxy and carbohexoxy.

Examples of Y are alkyl radicals having one to four carbon atoms, dimethylamino and preferably phenyl.

The radical D is derived from a diazotizable aromatic monoamine or diamine. For example amines of the benzene, naphthalene, azobenzene, phthalic acid, phthalimide, benzidine, terephthalic acid, diphenyl ether, diphenyl sulfide, diphenylamine, benzophenone, dibenzofuran, diphenylsulfone, diphenylmethane, diphenylurea or diphenylstilbene series are suitable.

The components may bear substituents which are customary in azo dyes and also sulfonic acid groups, carboxyl groups or a radical having the general formula:

$-SO_2-NH-SO_2-Y$ (as defined above).

The following specific substituents are given by way of example: fluoro, chloro, bromo, nitro, cyano, methyl, ethyl, methoxy, ethoxy, phenoxy, trifluoromethyl, acetylamino, benzoylamino, N-phenylcarbamoylamino, N-methylcarbamoylamino, hydroxy, acetyl, benzoyl, methylsulfonyl, ethylsulfonyl, phenylsulfonyl, arylazo, carboxy, carbalkoxy, carbophenoxy, carbamoyl, N-monosubstituted or N,N-disubstituted carbamoyl, and radicals having the formulae: $-SO_2-R^1$, $-O-SO_2-R^1$, $-SO_2-\underset{R^3}{N}-R^2$ or $-O-SO_2-\underset{R^3}{N}-R^2$ where $R^1$ denotes alkyl having one to four carbon atoms, phenyl or tolyl and $R^2$ and $R^3$ each denotes hydrogen or alkyl having one to four carbon atoms, or one of the radicals $R^2$ and $R^3$ denotes aryl.

The radicals $R^2$ and $R^3$ may form a ring with the nitrogen atom, with or without the inclusion of another hetero atom, for example a pyrrolidine, piperidine or morpholine ring.

Carbalkoxy radicals as substituents for the component D may contain for example the following alcohol components: methanol, ethanol, propanol, butanol, isobutanol, hexanol, ethylhexanol, cyclohexanol, benzyl alcohol, phenol, β-hydroxyethanol, β-methoxyethanol, β-ethoxyethanol or β-butoxyethanol or the compounds having the formulae: $HO-(CH_2CH_2O)$, $HO-(CH_2CH_2O)_2C_2H_5$, $HO-(CH_2CH_2O)_3CH_3$, $HO-(CH_2CH_2O)_3-C_2H_5$, $HOCH_2CH_2OCOCH_3$ and the compounds β-hydroxypropanol, γ-hydroxypropanol, δ-hydroxybutanol and ω-hydroxyhexanol.

Examples of N-monosubstituted or N,N-disubstituted carbamoyl radical are N-methylcarboxamido, N-ethylcarboxamido, N-butylcarboxamido, N-cyclohexylcarboxamido, n-(β-ethylhexyl)-carboxamido, N-β-hydroxyethylcarboxamido, N-β-methoxyethylcarboxamido, N-β-hydroxypropylcarboxamido, N-γ-hydroxypropylcarboxamido, N-γ-methoxypropylcarboxamido, N-ethoxypropylcarboxamido, N,N-dimethylcarboxamido, N,N-diethylcarboxamido, N,N-dipropylcarboxamido, N-methyl-N-β-hydroxyethylcarboxamido, pyrrolidido and morpholido.

The following specific aniline derivatives are given by way of example: aniline o-toluidine, m-toluidine, p-toluidine, o-nitraniline, m-nitraniline, p-nitraniline, o-cyanoaniline, m-cyanoaniline, p-cyanoaniline, p-chloroaniline, 3,4-dichloroaniline, 2,5-dichloroaniline, 2,4,5-trichloroaniline, 2-chloro-4-nitroaniline, 2-bromo-4-nitroaniline, 2-cyano-4-nitroaniline, 3-nitro-4-aminotoluidine, 3-hydroxyaniline, 4-methoxyaniline, N-acetyl-p-phenylenediamine, N-benzoyl-p-phenylenediamine, N-benzenesulfonyl-p-phenylenediamine, N-benzenesulfonyl-m-phenylenediamine, 4-aminodiphenylurea, 4-aminoacetophenone, 4-aminobenzophenone, 2-aminobenzophenone, 4-methylsulfonylaniline, 2-aminodiphenylsulfone, 4-aminoazobenzene, 3-methoxy-4-amino-6-methylazobenzene, 3,6-dimethoxy-4-aminobenzene, 2-aminobenzoic acid, 3-aminobenzoic acid, 4-aminobenzoic acid, eth methyl, ethyl, propyl, butyl, isobutyl, β-ethylhexyl, β-butoxyethyl, methyldiglycol, ethyldiglycol, methyltriglycol, ethyltriglycol, β-hydroxyethyl, β-acetoxyethyl, β-(β'-hydroxyethoxy)-ethyl, β-hydroxypropyl, γ-hydroxypropyl, δ-hydroxybutyl and ω-hydroxyhexyl, esters of 2-aminobenzoic acid, 3-aminobenzoic acid or 4-aminobenzoic acid, 4-nitroanthranilic acid and the methyl, isobutyl and methyldiglycol esters thereof, and the dimethyl, diethyl, dipropyl, dibutyl, diisobutyl, dimethylglycol, diethylglycol, dimethyldiglycol, diethyldiglycol and dibenzyl esters of 3-aminophthalic acid, 4-aminophthalic acid, 5-aminoisophthalic acid and aminoterephthalic acid.

The following are also suitable:

3 or 4 aminobenzoic acid -amide, -methylamide, -propylamide, -n-butylamide, -isobutylamide, -cyclohexylamide, -methoxypropylamide, -ethoxypropylamide, -β-hydroxyethylamide and -anilide, the dimethylamide, diethylamide, di-n-propylamide, pyrrolidide, morpholide and N-methyl-N-β-hydroxyethylamide of 2-aminobenzoic acid, 3-aminobenzoic acid or 4-aminobenzoic acid, the diamide, dimethylamide, dimethoxypropylamide and di-n-butylamide of 5-aminoisophthalic acid, the bis-dimethylamide or bis-diethylamide of 5-aminoisophthalic acid or of amino terephthalic acid, 3-aminophthalimide, 4-aminophthalimide or the β-hydroxyethylimide, γ-hydroxypropylimide, methylimide, n-butylimide, γ-methoxypropylimide or phenylimide of 3-aminophthalic acid or 4-aminophthalic acid, the amide, methylamide, ethylamide, propylamide, n-butylamide, isobutylamide, cyclohexylamide, γ-methoxypropylamide, β-hydroxyethylamide or anilide of 3-aminobenzenesulfonic acid or of 4-aminobenzenesulfonic acid, the dimethylamide, diethylamide, dipropylamide, pyrrolidide, morpholide, or N-methylanilide of 2-aminobenzenesulfonic acid, 3-aminobenzenesulfonic acid or 4-aminobenzenesulfonic acid, the 2'-aminophenyl, 3'-aminophenyl or 4'-aminophenyl ester of methylsulfonic acid, the 2'-aminophenyl, 3'-aminophenyl or 4-aminophenyl ester of ethylsulfonic acid, the 2'-aminophenyl, 3'-aminophenyl or 4'-aminophenyl 4'of butylsulfonic acid, the 2'-aminophenyl, 3'-aminophenyl or 4'-aminophenyl ester of benzenesulfonic acid, the 2'-aminophenyl, 3'-aminophenyl or 4'-aminophenyl ester of 4-methylbenzenesulfonic acid, the 2'-aminophenyl, 3'-aminophenyl or 4'-aminophenyl ester of 4-chlorobenzenesulfonic acid, the 2'-aminophenyl, 3'-aminophenyl or 4'-aminophenyl ester of dimethylaminosulfonic acid, the 2'-aminophenyl, 3'-aminophenyl or 4'-aminophenyl ester of di-n-butylaminosulfonic acid, the 3'-aminophenyl ester of morpholine N-sulfonic acid and the 3'-aminophenyl ester of N-methylaniline-N-sulfonic acid.

The following are also suitable:
o-aminobenzenesulfonic acid, m-aminobenzenesulfonic acid, p-aminobenzenesulfonic acid, 1-amino-2-chlorobenzene-5-sulfonic acid, 1-amino-4-chlorobenzene-3-sulfonic acid, 1-amino-4-chlorobenzene-2-sulfonic acid,
1-amino-3-chlorobenzene-6-sulfonic acid,
1-amino-2,5-dichlorobenzene-4-sulfonic acid,
1-amino-3,4-dichlorobenzene-6-sulfonic acid,
1-amino-2-nitrobenzene-4-sulfonic acid,
1-amino-4-nitrobenzene-2-sulfonic acid,
1-amino-3-chloro-4-methylbenzene-6-sulfonic acid,
1-amino-2-methylbenzene-4-sulfonic acid,
1-amino-2-methoxy-4-nitrobenzene-5-sulfonic acid,
1-amino-4-methylbenzene-2-sulfonic acid,
1-amino-2-methoxybenzene-5-sulfonic acid,
1-amino-2-methoxy-4-nitrobenzene-5-sulfonic acid,
3-acetamino-1-aminobenzene-2-sulfonic acid,
4-acetamino-1-aminobenzene-2-sulfonic acid,
1-amino-2,4-dimethylbenzene-5-sulfonic acid,
1-amino-4-ethoxybenzene-2-sulfonic acid,
1-aminobenzene-2,5-disulfonic acid,
1-aminobenzene-2,4-disulfonic acid,
1-aminonaphthalene-2-sulfonic acid,
1-aminonaphthalene-3-sulfonic acid,
1-aminonaphthalene-4-sulfonic acid,
1-aminonaphthalene-5-sulfonic acid,
1-aminonaphthalene-6-sulfonic acid,
1-aminonaphthalene-7-sulfonic acid,
1-aminonaphthalene-8-sulfonic acid,
2-aminonaphthalene-1-sulfonic acid,
2-aminonaphthalene-5-sulfonic acid,
2-aminonaphthalene-6-sulfonic acid,
2-aminonaphthalene-7-sulfonic acid,
2-aminonaphthalene-8-sulfonic acid,
1-aminonaphthalene-3,6-disulfonic acid,
2-aminonaphthalene-3,6-disulfonic acid,
2-aminonaphthalene-6,8-disulfonic acid,
1-amino-2-ethoxynaphthalene-6-sulfonic acid,
2-aminonaphthalene-4,7-disulfonic acid,
2-aminonaphthalene-4,8-disulfonic acid,
1-amino-4-nitrobenzene-2-methylsulfone,
1-aminobenzene-4-(p-tolyl)-sulfonamide,
3-aminophthalic acid p-tolylimide,
4-aminophthalic acid p-tolylimide,
3-aminophthalic acid p-tolylimidosulfonic acid,
4-aminophthalic acid p-tolylimidosulfonic acid,
3-aminophthalic acid-4'-chloro-2'-sulfonic acid tolylimide,
4-aminophthalic acid-4'-chloro-2'-sulfonic acid tolylimide,
4-aminodiphenyl,
4,4'-diaminodiphenyl-2,2'-disulfonic acid,
4,4'-diaminodiphenyl-3-sulfonic acid,
4,4'-diaminodiphenyl-3,4-disulfonic acid,
4,4'-diamino-3,3'-dimethoxydiphenyl,
4,4'-diaminodiphenylmethane,
4,4'-diamino-2,2'-dichlorodiphenylmethane,
4,4'-diamino-3,3'-dichlorodiphenylmethane,
4,4'-diaminostilbene,
4,4'-diaminostilbene-2,2'-disulfonic acid,
4-nitro-4-aminostilbene-2,2'-disulfonic acid,
p-aminodiphenylamine,
p-aminodiphenylamine-2-sulfonic acid,
4,4'-diaminodiphenylamine,
4,4'-diaminodiphenylamine-2-sulfonic acid,
4-methoxy-4'-aminodiphenylamine,
3-methoxy-4-aminodiphenylamine,
4,4'-diaminoazobenzene-2-sulfonic acid,
4-aminoazobenzene-3,4'-disulfonic acid,
4-amino-4'-nitroazobenzene,
4-aminoazobenzene-4'-sulfonic acid,
4-amino-3-methoxy-2'-chloro-4'-nitroazobenzene,
4-amino-3,2'-dimethylazobenzene,
4-amino-2,3'-dimethylazobenzene,
4-amino-3,2'-dimethylazobenzene-4'-sulfonic acid,
1-aminonaphthalene-4-azobenzene,
1-amino-2-ethoxynaphthalene-6-sulfonic acid-4-(azobenzene-2'-sulfonic acid),
1-amino-2-ethoxynaphthalene-6-sulfonic acid-4-(azobenzene-3'-sulfonic acid),
1-amino-2-ethoxynaphthalene-6-sulfonic acid-4-(azobenzene-4'-sulfonic acid),
4-amino-4'-chlorodiphenyl ether,
4,4'-diaminodiphenyl ether,
4,4'-diaminodiphenylsulfone,
4,4'-diaminodiphenyl sulfide,
4,4'-diaminodiphenyl sulfide-2,2'-disulfonic acid,
p-aminophenylbenzyl ether,
3-aminophthalic acid phenylimide,
4-aminophthalic acid phenylimide,
3-aminophthalic acid 4'-chlorophenylimide,
4-aminophthalic acid 4'-chlorophenylimide,
the imide, methylimide, propylimide, n-butylimide, β-hydroxypropylimide, (β-phenyl)-ethylimide and (β-

The following further dyes are obtained in a manner analogous to that described above using the diazo and coupling components in the following Table:

Coupling component structure:

$$\text{HO}-\underset{R}{N}=\underset{\underset{CH_3}{|}}{\overset{\overset{CO-NH_2}{|}}{C}}=O$$

(pyridone with CH₃, CO-NH₂, =O, HO, N-R substituents)

| Example | Diazo component | Coupling component | Shade of dyeing on polycaprolactam |
|---|---|---|---|
| 2 | O₂N–C₆H₃(SO₃H)–NH₂ | —R= —CH₃ | yellow |
| 3 | " | —C₂H₅ | yellow |
| 4 | " | —C₃H₇(n) | " |
| 5 | " | —C₅H₁₁(n) | " |
| 6 | " | —C₆H₁₃(n) | " |
| 7 | " | —CH₂CH₂CH₂OCH₃ | " |
| 8 | " | —CH₂CH₂CH₂OC₂H₅ | " |
| 9 | " | —C₆H₅ | " |
| 10 | " | —C₆H₄CH₃(p) | " |
| 11 | " | —C₆H₄Cl(p) | " |
| 12 | " | —C₆H₄OCH₃(p) | " |
| 13 | " | —CH₂C₆H₅ | " |
| 14 | " | —CH₂CH₂—OH | " |
| 15 | " | —CH₂CH₂—CH₂OH | " |
| 16 | HO₃S–C₆H₃(NO₂)–NH₂ | —C₄H₉(n) | " |
| 17 | " | —C₅H₁₁(n) | " |
| 18 | " | —C₆H₁₃(n) | " |
| 19 | " | —CH₂CH₂CH₂—OCH₃ | " |
| 20 | " | —CH₂CH₂CH₂—OC₂H₅ | " |
| 21 | " | —CH₂C₆H₅ | " |
| 22 | " | —C₆H₅ | " |
| 23 | " | —C₆H₄CH₃(p) | " |
| 24 | HO₃S–C₆H₃(NO₂)–NH₂ | —C₆H₄OCH₃(p) | yellow |
| 25 | " | —C₆H₄Cl(p) | " |
| 26 | " | —C₆H₁₁ (cyclohexyl) | " |
| 27 | HOOC–C₆H₄–NH₂ | —CH₂—CH₂CH₂CH₂CH₂CH₃ | " |
| 28 | " | —CH₂CH₂CH₂OCH₃ | " |
| 29 | " | —CH₂CH₂CH₂OC₂H₅ | " |
| 30 | " | —CH₂CH₂CH₂OH | " |
| 31 | H₂N–C₆H₄–S–C₆H₄–NH₂ | —C₆H₄SO₃H | orange |
| 32 | " | —CH₂C₆H₄SO₃H | " |
| 33 | H₂N–C₆H₄–O–C₆H₄–NH₂ | " | yellow |
| 34 | H₂N–C₆H₄–C₆H₄–NH₂ | " | orange |
| 35 | H₂N–C₆H₃(Cl)–C₆H₃(Cl)–NH₂ | —C₆H₄SO₃H | " | ethyl)-hexylimide of 3-aminophthalic acid or of 4-aminophthalic acid, the 1'-naphthylimide or 2'-naphthylimide of 3-aminophthalic acid or of 4-aminophthalic acid, the benzylimide, benzylsulfonimide or cyclohexylimide of 3-aminophthalic acid or of 4-aminophthalic acid, β-(3'-aminophthalylimido)-acetic acid or β-(4'-aminophthalylimido)-acetic acid or their alkyl esters, preferably the methyl esters.

In accordance with the foregoing description, D preferably represents phenyl substituted by sulfonic acid or the same sulfophenyl further substituted by chlorine, bromine, methyl, ethyl or acetylamino; naphthyl substituted once or twice by sulfonic acid; phenyl substituted by carboxylic acid or the same carboxylphenyl further substituted by chlorine or bromine; or phenyl substituted by chlorine, bromine, cyano, trifluoromethyl, methyl, ethyl, carboalkoxy of 2 to 5 carbon atoms, carbamoyl, N-alkylcarbamoyl of 1 to 8 carbon atoms in said alkyl, N,N-dialkyl-carbamoyl of 1 to 4 carbon atoms in each alkyl, sulfamoyl, N-alkyl-sulfamoyl of 1 to 8 carbon atoms in said alkyl, N,N-dialkyl-sulfamoyl of 1 to 4 carbon atoms in each alkyl, N-phenylcarbamoyl, N-tolylcarbamoyl, N-(hydroxysulfonyl)-phenyl carbamoyl, N-(hydroxysulfonyl)tolylcarbamoyl, N-phenyl-sulfamoyl, N-tolylsulfamoyl, N-(hydroxysulfonyl)-phenyl sulfamoyl or N-(hydroxysulfonyl)-tolylsulfamoyl.

Special industrial significance attaches to dyes having the general formula (Ia):

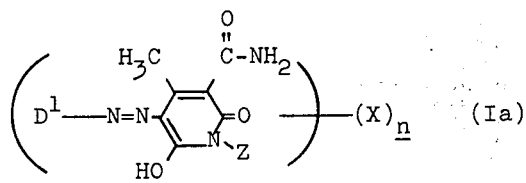

where
Z denotes alkyl having one to six carbon atoms, benzyl or a benzylsulfonic acid radical;
$n$ denotes one of the integers 1 and 2;
$D^1$ phenyl substituted by sulfonic acid or the same sulfophenyl further substituted by chlorine, bromine, methyl or ethyl; phenyl substituted by carboxylic acid or the same carboxylphenyl further substituted by chlorine or bromine; or naphthyl substituted once or twice by sulfonic acid, with the proviso that $D^1$ and Z together contain at least one sulfonic or carboxylic group.
X has the meanings given above.
Particularly valuable dyes are those having the following alkyl radicals:
CH₃, C₂H₅, n-C₃H₇, iso-C₃H₇, n-C₄H₉, n-C₆H₁₃ and

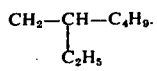

The new dyes are yellow to red and on synthetic polyamides (for example polycaprolactam) and wool give yellow to red dyeings which exhibit very good fastness properties; dyes having carboxyl group but are devoid of sulfonic groups also go onto polyesters.

The new dyes may be manufactured by reacting a diazo or tetrazo compound of an amine having the general formula:

D—(NH₂)ₘ with a coupling component having the general formula:

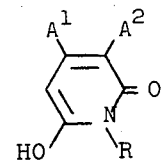

(A¹, A², D, $m$ and R having the meanings given above) at least one of the components bearing at least one water-solubilizing group.

Coupling is carried out as usual in aqueous medium with or without the addition of solvents in the weakly acid or weakly alkaline range.

Another possibility for the manufacture of the water-soluble dyes having the general formula (I) with X denoting —SO₃H is the sulfonation of the water-insoluble azo dyes having the general formula (III):

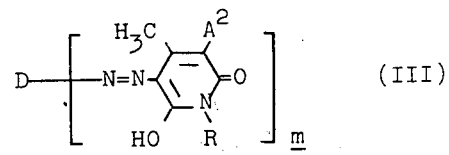

in which A², D, $m$ and R have the meanings given in the general formula (I) with 20 to 50% oleum.

The following Examples illustrate the invention. References to parts and percentages in the following Examples are by weight unless otherwise specified.

EXAMPLE 1

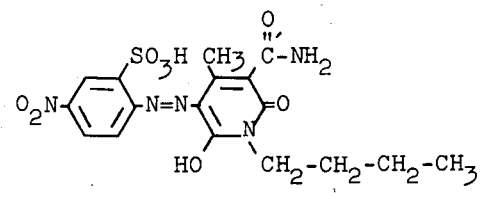

150 parts of water and 15 parts by volume of 30% hydrochloric acid are added to 10.9 parts of 4-nitraniline-2-sulfonic acid and the whole is stirred for fifteen minutes. Then 75 parts of ice and 16 parts by volume of 23% sodium nitrite solution is added, stirring is continued for two hours at 0° to 5°C and then any excess of nitrous acid present is removed in the usual way. The diazonium salt mixture is then added in portions to a solution, cooled to 0°C, of 11.6 parts of 1-n-butyl-2-hydroxy-3-carboxamido-4-methylpyridone-(6) in 300 parts of water, 5 parts of 50% caustic soda solution and 5 parts of sodium carbonate. When coupling is complete, the dye is precipitated by adding 30 parts of sodium chloride, suction filtered, washed with 10% sodium chloride solution until neutral and dried at 130°C. It is obtained in the form of a yellow powder which dissolves in water giving a yellow color.

The shade of the dyeing on polycaprolcatam is pure yellow.

-continued

Coupling component structure (header):

pyridine with CH₃, CO-NH₂, =O, HO, N-R substituents

| Example | Diazo component | Coupling component | Shade of dyeing on polycaprolactam |
|---------|-----------------|--------------------|-----------------------------------|
| 36 | H₂N-C₆H₄-NH-C(=O)-NH-C₆H₄-NH₂ (with H, O, H shown) | " | red |
| 37 | H₂N-C₆H₄-CH₂-C₆H₄-NH₂ | " | yellow |
| 38 | H₂N-C₆H₄-NH-C₆H₄-NH₂ | " | red |
| 39 | H₂N-C₆H₄-N=N-C₆H₄-NH₂ | —C₆H₄SO₃H | red |
| 40 | " | —CH₂C₆H₄SO₃H | red |
| 41 | | SO₃H-C₆H₃-CH₃ | " |
| 42 | H₂N-C₆H₄-C(=O)-C₆H₄-NH₂ | " | yellow |
| 43 | " | —CH₂C₆H₄SO₃H | " |
| 44 | H₂N-C₆H₄-S(=O)(=O)-C₆H₄-NH₂ | —CH₂C₆H₄SO₃H | yellow |
| 45 | " | —C₆H₄SO₃H | " |
| 46 | H₂N-C₆H₄-CH₂-C₆H₄-NH₂ | C₆H₃(CH₃)(SO₃H) | " |
| 47 | " | —CH₂C₆H₄SO₃H | " |
| 48 | C₆H₅-NH₂ | —C₆H₄SO₃H | " |
| 49 | " | —CH₂C₆H₄SO₃H | " |
| 50 | 2-Cl-C₆H₄-NH₂ | —C₆H₄SO₃H | " |
| 51 | Cl-C₆H₄-NH₂ | " | " |

-continued
Coupling component (header structure):
$$\begin{array}{c} CH_3 \quad CO-NH_2 \\ \diagup \\ N=O \\ HO \quad R \end{array}$$
| Example | Diazo component | Coupling component | Shade of dyeing on polycaprolactam |
|---------|-----------------|--------------------|-----------------------------------|
| 52 | 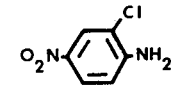 | —$C_6H_4SO_3H$ | yellow |
| 53 | 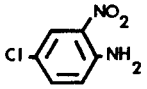 | " | " |
| 54 | 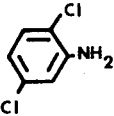 | " | " |
| 55 |  | " | " |
| 56 | 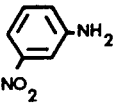 | " | greenish yellow |
| 57 | 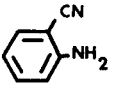 | " | " |
| 58 | 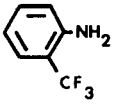 | —$C_6H_4SO_3H$ | yellow |
| 59 | 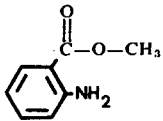 | " | greenish yellow |
| 60 | 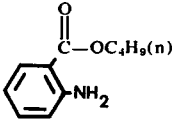 | " | " |
| 61 | 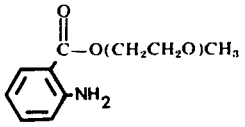 | " | " |

-continued
| Example | Diazo component | Coupling component | Shade of dyeing on polycaprolactam |
|---|---|---|---|
| 62 | 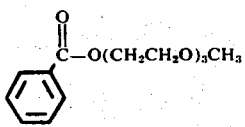 | '' | '' |
| 63 | 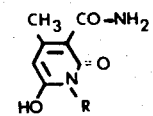 | —$C_6H_4SO_3H$ | greenish yellow |
| 64 | 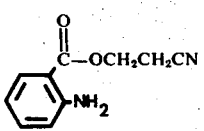 | '' | '' |
| 65 | 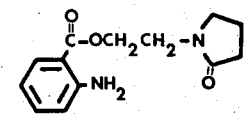 | '' | '' |
| 66 | 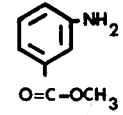 | '' | '' |
| 67 | 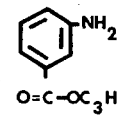 | '' | '' |
| 68 | 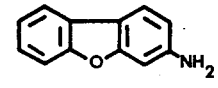 | 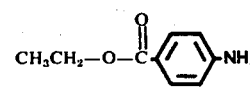 | yellow |
| 69 | 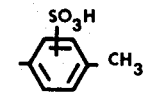 | '' | '' |
| 70 | 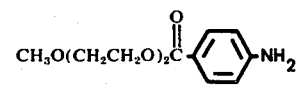 | '' | '' |
| 71 | 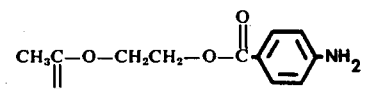 | '' | '' |
Coupling component structure (header):
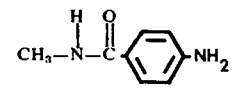

-continued

| Example | Diazo component | Coupling component (CH₃, CO—NH₂ pyridone with HO, N=O, R) | Shade of dyeing on polycaprolactam |
|---|---|---|---|
| 72 | (CH₃)₂N—CO—C₆H₄—NH₂ | '' | '' |
| 73 | n-C₄H₉—NH—CO—C₆H₄—NH₂ | '' | '' |
| 74 | CH₃—OCH₂CH₂CH₂—NH—CO—C₆H₄—NH₂ | —C₆H₃(SO₃H)(CH₃) | yellow |
| 75 | CH₃CH₂CH₂CH(CH₂CH₃)—CH₂—NH—CO—C₆H₄—NH₂ | —C₆H₄SO₃H | yellow |
| 76 | H₂N—O₂S—C₆H₄—NH₂ | '' | '' |
| 77 | 3-SO₂NH₂-C₆H₄-NH₂ | '' | '' |
| 78 | 3-SO₂NHC₄H₉(n)-C₆H₄-NH₂ | '' | '' |
| 79 | (CH₃)₂N—O₂S—C₆H₄—NH₂ | '' | '' |
| 80 | CH₃CH₂CH₂CH₂CHCH₂N—O₂S—C₆H₄—NH₂ | '' | '' |
| 81 | C₆H₅—NH—O₂S—C₆H₄—NH₂ | '' | '' |
| 82 | 3-SO₂NHCH₂CH₂CH₂OCH₃-C₆H₄-NH₂ | '' | '' |
| 83 | CH₃CH₂—O—CO—C₆H₄—NH₂ | —CH₂C₆H₄SO₃H | '' |
| 84 | 3-SO₂N(CH₃)₂-C₆H₄-NH₂ | '' | '' |

-continued

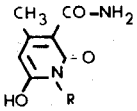

| Example | Diazo component | Coupling component | Shade of dyeing on polycaprolactam |
|---|---|---|---|
| 85 |  | —CH₂C₆H₄SO₃H | yellow |
| 86 |  | " | " |

EXAMPLE 87

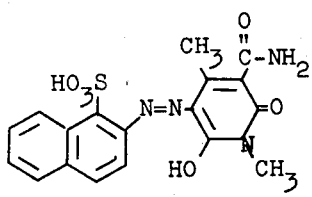

75 parts of water, 6 parts of sodium carbonate and 15 parts by volume of 23% sodium nitrite solution are added to 11.2 parts of 2-aminonaphthalene-1-sulfonic acid. The mixture is added in portions to a mixture of 75 parts of ice and 13 parts by volume of 30% hydrochloric acid and the whole is stirred for two hours at 0° to 5°C. Any excess of nitrous acid present is then removed as usual and the diazonium salt mixture is added in portions to a solution, cooled to 0°C, of 9.5 parts of 1-methyl-2-hydroxy-3-carboxamido-4-methylpyridone-(6) in 300 parts of water, 5 parts of 50% caustic soda solution and 6 parts of sodium carbonate. When coupling has ended, 30 parts of sodium chloride and then 30% acetic acid are added to the mixture until it has a pH of from 6 to 7. The deposited dye is filtered off, washed neutral with 10% sodium chloride solution and dried. An orange powder is obtained which dissolves in water with a yellow color.

The shade of the dyeing on polycaprolactam is golden yellow.

Other dyes having similar properties are obtained by using the compounds set out in the following Table instead of the diazo and coupling components mention in Example 87:

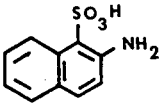

| Example | Diazo component | Coupling component | Shade of dyeing on polycaprolactam |
|---|---|---|---|
| 88 | | —C₈H₁₇(i) | golden yellow |
| 89 | " | —C₄H₉(n) | " |
| 90 | " | —C₅H₁₁(n) | " |
| 91 | " | —C₆H₁₃(n) | " |

-continued

Coupling component structure:

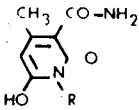

| Example | Diazo component | Coupling component | Shade of dyeing on polycaprolactam |
|---|---|---|---|
| 92 | " | —CH₂CH₂CH₂OH | " |
| 93 | " | —CH₂CH₂CH₂OC₂H₅ | " |
| 94 | " | —CH₂CH₂C₆H₅ | yellow |
| 95 | " | —C₆H₅ | " |
| 96 | " | —C₆H₄CH₃ | " |
| 97 | 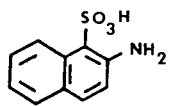 | —C₆H₄OCH₃(p) | " |
| 98 | " | —CH₂CH₂CH₂OCH(CH₃)₂ | " |
| 99 | 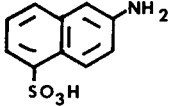 | —CH₂CH₂CH₂OCH₃ | golden yellow |
| 100 | " | —C₆H₄OCH₃(p) | yellow |
| 101 | 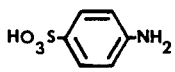 | —CH₂CH₂CH₂CH₃ | greenish yellow |
| 102 | " | —CH₂CH₂CH₂—OH | " |
| 103 | " | —CH₂CH₂CH₂—OCH₃ | " |
| 104 | " | —CH₂CH₂CH₂—OC₂H₅ | " |
| 105 | " | —CH₂C₆H₅ | yellow |
| 106 | " | —C₆H₅ | " |
| 107 | 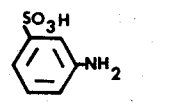 | —CH₂CH₂CH₂CH₃ | greenish yellow |
| 108 | " | —CH₂CH₂CH₂OH | " |
| 109 | " | —CH₂CH₂CH₂OC₂H₅ | " |
| 110 | " | —CH₂C₆H₅ | " |
| 111 | " | —C₆H₅ | yellow |
| 112 | " | —C₆H₄CH₃ | yellow |
| 113 | 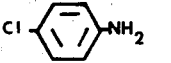 | —C₄H₉(n) | golden yellow |
| 114 | " | —C₅H₁₁(n) | " |
| 115 | " | —C₆H₁₃(n) | " |
| 116 | " | —CH₂CH₂CH₂OH | " |
| 117 | 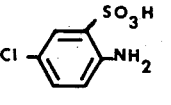 | —CH₂CH₂CH₂OCH₃ | " |
| 118 | " | —CH₂C₆H₅ | yellow |
| 119 | " | —C₆H₄OCH₃(p) | yellow |
| 120 | " | —C₆H₄OCH₃(p) | " |
| 121 | 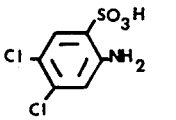 | —C₄H₉(n) | " |
| 122 | " | —C₅H₁₁(n) | " |
| 123 | " | —C₆H₁₃(n) | " |
| 124 | " | —CH₂C₆H₅ | " |
| 125 | " | —CH₂CH₂CH₂OCH₃ | " |
| 126 | " | —C₆H₅ | " |

-continued

Coupling component structure:

$$\text{HO}-\underset{\underset{R}{|}}{N}=\underset{\underset{}{||}}{C}\text{(pyridone with CH}_3\text{, CO-NH}_2\text{, =O)}$$

| Example | Diazo component | Coupling component | Shade of dyeing on polycaprolactam |
|---|---|---|---|
| 127 | CH₃-C₆H₃(SO₃H)(NH₂) | —C₅H₁₁(n) | yellow |
| 128 | " | —C₆H₁₃(n) | " |
| 129 | " | —CH₂CH₂CH₂OCH₃ | " |
| 130 | " | —CH₂CH₂CH₂OH | " |
| 131 | " | —CH₂C₆H₅ | " |
| 132 | " | —C₆H₅ | " |
| 133 | " | —C₆H₄CH₃ | " |
| 134 | CH₃CH₂-C₆H₃(NH₂)(SO₃H) | —C₃H₇(n) | " |
| 135 | " | —C₄H₉(n) | " |
| 136 | " | —C₅H₁₁(n) | " |
| 137 | " | —C₆H₁₃(n) | " |
| 138 | " | —CH₃ | " |
| 139 | CH₃CH₂CH₂-C₆H₃(NH₂)(SO₃H) | —CH₃ | " |
| 140 | H₉C₄-C₆H₃(SO₃H)(NH₂) | —CH₃ | " |
| 141 | H₁₃C₆-C₆H₃(NH₂)(SO₃H) | —CH₃ | yellow |
| 142 | " | —C₂H₅ | " |
| 143 | " | —C₃H₇(n) | " |
| 144 | " | —C₃H₇(iso) | " |
| 145 | C₆H₄(SO₃H)(NH₂) | —C₅H₁₁(n) | greenish yellow |
| 146 | " | —C₆H₁₃(n) | " |
| 147 | " | —CH₂CH₂CH₂OCH₃ | " |
| 148 | " | —CH₂CH₂CH₂OC₂H₅ | " |
| 149 | " | —CH₂C₆H₅ | yellow |
| 150 | " | —C₆H₄CH₃ | " |
| 151 | " | —C₆H₄OCH₃(p) | " |
| 152 | " | —C₆H₅ | " |
| 153 | CH₃-C₆H₂(Cl)(SO₃H)(NH₂) | —C₃H₇(n) | yellow |
| 154 | " | —C₄H₉(n) | " |

-continued

Coupling component structure:

3-methyl-4-carbamoyl-6-hydroxy-pyridone with =O and N-R, HO substituents (CH₃, CO-NH₂ on ring, =O, N-R, HO)

| Example | Diazo component | Coupling component | Shade of dyeing on polycaprolactam |
|---------|----------------|-------------------|-----------------------------------|
| 155 | " | $-C_5H_{11}(n)$ | " |
| 156 | " | $-C_6H_{13}(n)$ | " |
| 157 | " | $-CH_2CH_2CH_2OH$ | " |
| 158 | " | $-CH_2CH_2CH_2OCH_3$ | " |
| 159 | " | $-CH_2CH_2CH_2OC_2H_5$ | " |
| 160 | " | $-CH_2C_6H_5$ | " |
| 161 | 2-amino-4-chloro-5-methylbenzenesulfonic acid (CH₃, Cl, NH₂, SO₃H on benzene) | $-C_6H_5$ | " |
| 162 | " | $-C_6H_4CH_3$ | " |
| 163 | 2-amino-3,5-dichloro-benzenesulfonic acid (HO₃S, Cl, NH₂, Cl on benzene) | $-C_5H_{11}(n)$ | greenish yellow |
| 164 | " | $-C_6H_{13}(n)$ | " |
| 165 | " | $-CH_2CH\ 2CH_2-OH$ | " |
| 166 | " | $-CH_2CH_2CH_2-O-CH_3$ | " |
| 167 | " | $-CH_2CH_2CH_2-O-C_2H_5$ | " |
| 168 | " | $CH_2C_6H_5$ | yellow |
| 169 | " | $-C_6H_5$ | " |
| 170 | " | $-C_6H_4CH_3$ | " |
| 171 | " | $-C_6H_4Cl(p)$ | " |
| 172 | " | cyclohexyl (H) | " |
| 173 | 4-acetamido-2-amino-benzenesulfonic acid (CH₃CO-NH, SO₃H, NH₂ on benzene) | $-CH_3$ | orange |
| 174 | " | $-C_2H_5$ | " |
| 175 | " | $-C_3H_7(n)$ | " |
| 176 | " | $-C_4H_9(n)$ | " |
| 177 | 4-acetamido-2-amino-benzenesulfonic acid (CH₃CO-NH, SO₃H, NH₂ on benzene) | $-C_5H_{11}(n)$ | orange |
| 178 | " | $-C_6H_{13}(n)$ | " |
| 179 | " | $-CH_3CH_2OH$ | " |
| 180 | " | $-CH_2CH_2CH_2OH$ | " |
| 181 | " | $-CH_2CH_2CH_2OCH_3$ | " |
| 182 | " | $-CH_2CH_2CH_2OC_2H_5$ | " |
| 183 | " | $-CH_2C_6H_5$ | " |
| 184 | " | $-C_6H_5$ | " |
| 185 | " | $-C_6H_4CH_3$ | " |
| 186 | " | $-C_6H_4OCH_3(p)$ | " |
| 187 | " | $-C_6H_4Cl$ | " |
| 188 | 4-aminobenzoic acid (HO-CO, NH₂ on benzene) | $-CH_3$ | greenish yellow |
| 189 | " | $-C_2H_5OH$ | " |
| 190 | 5-aminoisophthalic acid (HOOC, NH₂, HOOC on benzene) | $-CH_3$ | greenish yellow |

-continued

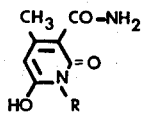

| Example | Diazo component | Coupling component | Shade of dyeing on polycaprolactam |
|---|---|---|---|
| 191 | (3,5-dicarboxyaniline) | —C₂H₅ | " |
| 192 | " | —C₂H₅OH | " |
| 193 | " | —C₃H₇(n) | " |
| 194 | " | —CH₂CH₂CH₂OH | " |

(In the next five examples, a different coupling component is shown complete.)

| Example | Diazo component | Coupling component | Shade of dyeing on polycaprolactam |
|---|---|---|---|
| 195 | 4-(methylamino)-2-aminobenzenesulfonic acid | 4-methyl-3-(n-butoxycarbonyl)-6-hydroxy-1-methyl-2-pyridone | orange |
| 196 | " | 4-methyl-3-(n-butoxycarbonyl)-6-hydroxy-1-ethyl-2-pyridone | " |
| 197 | 4-methyl-2-aminobenzenesulfonic acid | 4-propyl-3-carbamoyl-6-hydroxy-1-phenyl-2-pyridone | yellow |
| 198 | 2-aminobenzene-1,4-disulfonic acid | " | " |

| Example | Diazo component | Coupling component | Shade of dyeing on polycaprolactam |
|---------|-----------------|--------------------|-----------------------------------|
| 199 | (structure: benzene with SO₃H, NH₂, SO₃H) | (structure: pyridone with CH₃, C(O)NH₂, HO, N-CH₂-C₆H₄-OCH₃) | yellow |

EXAMPLE 200

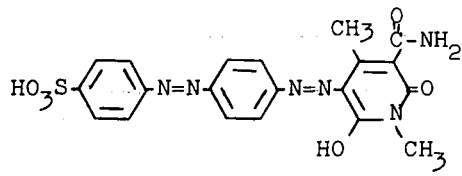

15.7 parts of 4-aminoazobenzene-4'-sulfonic acid is dissolved in 300 parts of hot water and 4 parts of 50% caustic soda solution and then at 40° to 50°C 16 parts by volume of 23% sodium nitrite solution is added to the solution and the mixture is introduced in portions into a mixture of 23 parts of 30% hydrochloric acid and 200 parts of ice. The mixture is stirred for two hours at 0° to 5°C and any excess of nitrous acid present is then destroyed as usual. The diazonium salt mixture is added to a solution, cooled to 0°C, of 9.5 parts of 1,4-dimethyl-2-hydroxy-3-carboxamidopyridone-(6) in 300 parts of water, 5 parts of 50% caustic soda solution and 12 parts of sodium carbonate. After coupling is over, the dye is precipitated by adding 20 parts of sodium chloride, suction filtered, washed neutral with 10% sodium chloride solution and dried.

A red powder is obtained which dissolves in water with an orange color.

The color of the dyeing on polycaprolactam is orange.

Other dyes are obtained by an analogous method using the diazo and coupling components of the following Table: diazonium -hydroxy-

| Example | Diazo component | Coupling component | Shade of dyeing on polycaprolactam |
|---------|-----------------|--------------------|-----------------------------------|
| 201 | HO₃S–C₆H₄–N=N–C₆H₄–NH₂ | R= —$C_2H_5$ | orange |
| 202 | " | —$C_3H_7(n)$ | " |
| 203 | " | —$C_4H_9(n)$ | " |
| 204 | " | —$C_5H_{11}(n)$ | " |
| 205 | " | —$C_6H_{13}(n)$ | " |
| 206 | " | —$CH_2CH_2OH$ | " |
| 207 | " | —$CH_2CH_2CH_2OH$ | " |
| 208 | " | —$CH_2CH_2CH_2OCH_3$ | " |
| 209 | " | —$C_6H_5$ | |
| 210 | " | —$C_6H_4CH_3$ | " |
| 211 | HO₃S–C₆H₄–N=N–C₆H₃(SO₃H)–NH₂ | —$C_6H_5$ | orange |
| 212 | " | —$CH_2CH_2C_6H_5$ | " |
| 213 | " | —$C_6H_4OCH_3(p)$ | " |
| 214 | " | —$C_6H_4Cl(p)$ | " |

-continued

| Example | Diazo component | Coupling component ![structure: CH3, CO-NH2, =O, HO, N-R on pyridone] | Shade of dyeing on polycaprolactam |
|---|---|---|---|
| 215 | H2N-C6H3(SO3H)-CH=CH-C6H3(SO3H)-NH2 | —CH2C6H5 | red |

In the next five examples, a different coupling component is shown complete.

| Example | Diazo component | Coupling component | Shade of dyeing on polycaprolactam |
|---|---|---|---|
| 216 | HO3S—C6H4—N=N—C6H4—NH2 | CH3, C-OC4H9 (n), =O, HO, CH3 pyridone | orange |
| 217 | HO3S—C6H4—N=N—C6H3(SO3H)—NH2 | CH3, CN pyridone, N-phenyl, HO | '' |
| 218 | '' | CH3, CN pyridone, N-(tolyl-CH3), HO | '' |
| 219 | '' | CH3, CN pyridone, N-(C6H4-OCH3), HO | '' |
| 220 | HO3S—naphthyl(OC2H5)(NH2)(SO3H)—N=N—C6H4—SO3H | R= —CH3 | red |
| 221 | '' | —C6H5 | red |

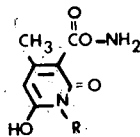

| Example | Diazo component | Coupling component | Shade of dyeing on polycaprolactam |
|---|---|---|---|
| 222 |  | —CH$_2$C$_6$H$_5$ | red |
| 223 | " | —CH$_3$ | red |
| 224 | " | —C$_4$H$_9$(n) | red |

EXAMPLE 225

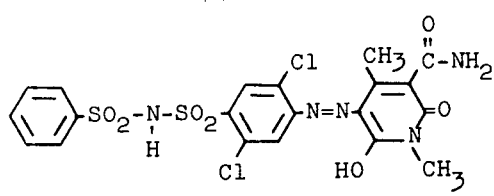

19 parts of 2,5-dichloroaniline-4-sulfonic acid (benzenesulfonyl)-amide is dissolved hot in 50 parts of dimethylformamide and 50 parts of water and after cooling, united with a mixture of 100 parts of water, 100 parts of ice and 15 parts by volume of 30% hydrochloric acid. 15 parts by volume of 23% sodium nitrite solution is then allowed to flow in during 15 minutes, the whole is stirred for another 45 minutes and any excess of nitrous acid present is destroyed as usual. The diazonium salt mixture is added in small portions to a solution, cooled to 0°C, of 9.5 parts of 1,4-dimethyl-2-hydroxy-3-carboxamidopyridone-(6) in 300 parts of water, 5 parts of 50% caustic soda solution and 7 parts of sodium carbonate. When coupling is completed, the dye formed is filtered off, washed until neutral with 10% sodium chloride solution and dried at 70°C. A yellow powder is obtained which dissolves in water giving a yellow color.

The color of the dyeing on polycaprolactam is greenish yellow.

Other dyes are obtained analogously to the said method from the coupling components and diazo components in the following Table.

| Example | Diazo component | Coupling component | Shade of dyeing on polycaprolactam |
|---|---|---|---|
| 226 |  | R= —CH$_3$ | yellow |

(In the next two examples, a different coupling component is shown complete.)

| | | | |
|---|---|---|---|
| 227 | " | 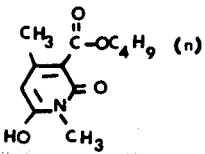 | " |
| 228 | 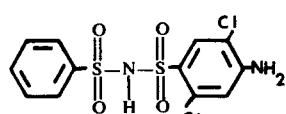 | " | " |

EXAMPLE 229

17.8 parts of 3-aminophthalic acid-(4'-chlorophenyl-imidosulfonic acid) is dissolved in 50 parts of dimethylformamide. The solution is introduced into a mixture of 150 parts of ice-water and 15 parts by volume of 30% hydrochloric acid and then 100 parts of ice and 15 parts by volume of 23% sodium nitrite solution are quickly added. After the whole has been stirred for two hours, any excess of nitrous acid present is removed as usual and the diazonium salt mixture is added in small portions to a solution, cooled to 0°C, of 9.5 parts of 1,4-dimethyl-2-hydroxy-3-carboxamidopyridone-(6) in 300 parts of water, 5 parts of 50% caustic soda solution and 7 parts of sodium carbonate.

After coupling is finished, the dye formed is precipitated by adding 30 parts of sodium chloride, suction filtered, washed with 10% sodium chloride solution and dried at 70°C.

The compound having the formula:

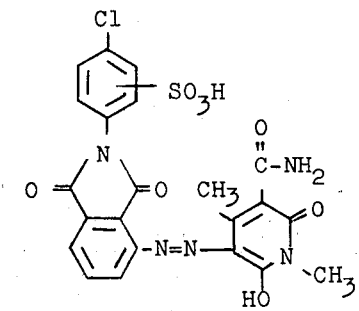

is obtained, the crystals thereof dissolving in water to give a yellow orange color.

The shade of the dyeing on polycaprolactam is yellow.

Other dyes are obtained analogously using the diazo and coupling components in the following Table.

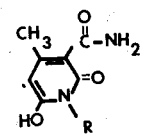

| Example | Diazo component | Coupling component | Shade of dyeing on polycaprolactam |
|---|---|---|---|
| 230 | (structure: benzene with $SO_3H$, $CH_3$, and phthalimide) | R= —$CH_3$ | yellow |
| 231 | " | —$C_2H_5$ | " |
| 232 | " | —$C_3H_7(n)$ | " |
| 233 | " | —$C_4H_9(n)$ | " |
| 234 | " | —$C_5H_{11}(n)$ | " |
| 235 | " | —$C_6H_{13}(n)$ | " |
| 236 | " | —H | " |
| 237 | " | —$CH_2CH_2$—OH | " |
| 238 | " | —$CH_2CH_2CH_2OH$ | " |
| 239 | " | —$CH_2CH_2CH_2$—$OCH_3$ | " |
| 240 | " | —$CH_2CH_2CH_2OC_2H_5$ | " |
| 241 | " | —$CH_2C_6H_5$ | " |
| 242 | (structure: benzene with $SO_3H$, $CH_3$, phthalimide with $NH_2$) | —$C_6H_5$ | yellow |
| 243 | " | —$C_6H_4CH_3$ | " |
| 244 | " | —$C_6H_4Cl$ | " |
| 245 | (structure: diphenylurea with $NH_2$) | —$C_6H_4SO_3H$ | " |

-continued

| Example | Diazo component | Coupling component | Shade of dyeing on polycaprolactam |
|---|---|---|---|
| | | 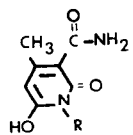 | |
| 246 | 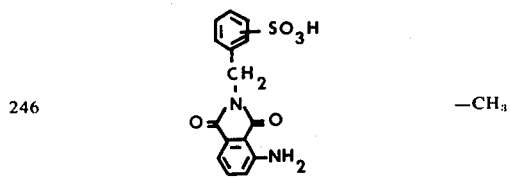 | —CH₃ | " |
| 247 | 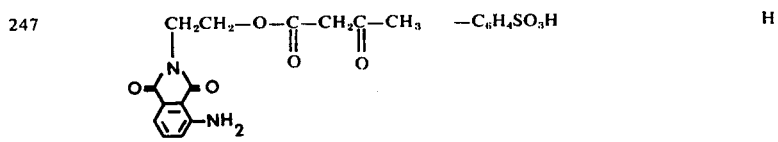 | —C₆H₄SO₃H | H |

EXAMPLE 248

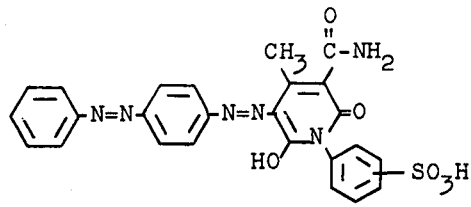

19.6 parts of p-aminobenzene is stirred at room temperature for several hours with 300 parts by volume of water and 0.3 part of the reaction product of oleylamine and about 12 moles of ethylene oxide. 25 parts by volume of 30% hydrochloric acid and 300 parts of ice are then added and 30 parts by volume of 23% sodium nitrite solution is allowed to flow in slowly at 0° to 5°C. Stirring is continued at the same temperature for another two hours and any excess of nitrous acid present is then removed by adding sulfamic acid. Coupling with 38.8 parts of N-phenylsulfonic acid-2-hydroxy-3-carboxamido-4-methylpyridone-(6) is carried out analogously to the method described in Example 1. A red dye is formed which dissolves in water with an orange red color.

The shade of the dyeing on polycaprolactam is orange red.

Other dyes are obtained by analogous procedures using the following diazo and coupling components:

| Example | Diazo component | Coupling component R | Shade of dyeing on polycaprolactam |
|---|---|---|---|
| 249 | 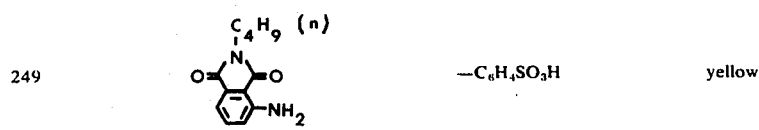 | —C₆H₄SO₃H | yellow |
| 250 |  | —C₆H₄SO₃H | " |

| Example | Diazo component | Coupling component R | Shade of dyeing on polycaprolactam |
|---|---|---|---|
| 251 | [structure: phthalimide with N-CH₂CH₂OH and NH₂] | " | " |
| 252 | [structure: phenyl-N=N-aryl with OCH₃, NH₂, CH₃] | " | orange |
| 253 | " | —CH₂C₆H₄SO₃H | orange |
| 254 | [structure: phthalimide with N-CH₂CH₂OH and NH₂] | " | yellow |

EXAMPLE 255

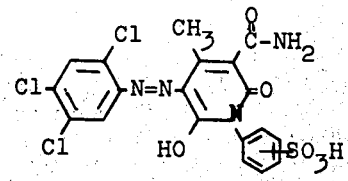

6.9 parts of solid sodium nitrite is introduced into 100 parts of concentrated sulfuric acid at 0°C to 10°C. The whole is heated at 70°C until a solution has been formed. The solution is cooled and 19.6 parts of 2,4,5-trichloroaniline is introduced into the solution at 0° to 5°C. The whole is stirred for 2 hours, 100 parts of ice is added while stirring, filtration is carried out and the solution is freed from any excess nitrous acid by adding sulfamic acid and allowed to flow into a solution of 11.7 parts of N-phenylsulfonic acid-2-hydroxy-3-carboxamido-4-methylpyridone-(6), 3parts of 50% caustic soda solution and 4 parts of sodium carbonate in 200 parts by volume of water, a pH of 7 to 8 and a temperature of 0° to 5°C being maintained by simultaneous addition of 50% caustic soda solution, 500 parts of ice, 50 parts of sodium chloride and cooling. The whole is stirred overnight. The deposited dye is suction filtered, washed with 10% sodium chloride solution and dried. A yellow powder is obtained which dissolves in water with a yellow color.

The shade of the dyeing on polycaprolactam is yellow.

Other dyes are obtained by analogous procedures from the diazo and coupling component in the following Table:

| Example | Diazo component | Coupling component R = | Shade of dyeing on polycaprolactam |
|---|---|---|---|
| 256 | [structure: phenyl with NH₂ and NO₂] | —C₆H₄SO₃H | yellow |
| 257 | " | " | " |
| 258 | " | [structure: phenyl with SO₃H and CH₃] | " |

EXAMPLE 259

9 parts of the dye having the formula:

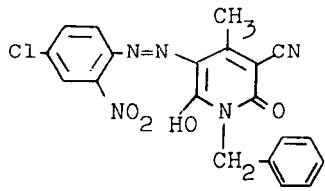

is introduced in portions into 48 parts of 23% oleum while stirring at 20°C. The mixture is heated to 30°C, stirred for two hours at this temperature, cooled to 20°C and poured with efficient stirring onto 100 parts of crushed ice. The precipitated dye is filtered off and dissolved in a little water at 40° to 50°C. The pH of the solution is adjusted to 4 to 6 with 20% caustic soda solution, then 130 parts of saturated sodium chloride solution is added while stirring and the mixture is allowed to cool to 20°C. The deposited dye having the formula:

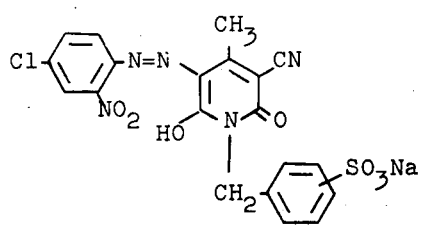

is filtered off and dried at 70°C. The red brown powder obtained dissolves in water with an orange color.

The shade of the dyeing on polycaprolactam is yellow.

EXAMPLE 260

10 parts of the dye having the formula

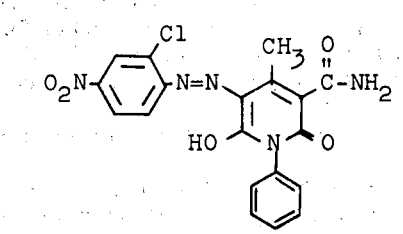

is introduced in portions into 50 parts of 23% oleum at 20°C. The mixture is heated to 30°C, stirred for two hours at this temperature, cooled to 20°C and the solution is poured onto 100 parts of crushed ice. The deposited dye is filtered off and dissolved in a little water at 40° to 50°C. The pH of the solution is adjusted to 4 to 6 by adding 20% caustic soda solution, then 130 parts of saturated sodium chloride solution is added while stirring and the mixture is allowed to cool to 20°C. The deposited dye having the formula:

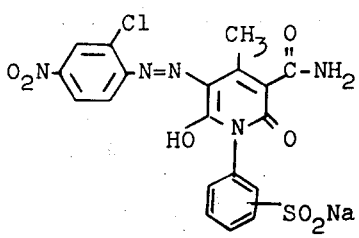

is filtered off and dried at 70°C. The red brown powder obtained dissolves in water with an orange color.

The color of the dyeing on polycaprolactam is yellow.

EXAMPLE 261

10 parts of the dye having the formula:

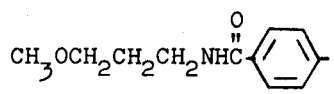

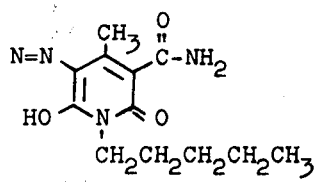

is introduced in portions into 50 parts of 23% oleum while stirring at 20°C. The mixture is heated to 30°C and stirred for two hours at this temperature. After cooling to 20°C, the solution is poured onto 100 parts of crushed ice. The dye having the formula:

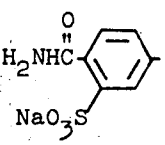

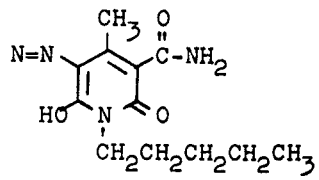

is isolated as usual.

An orange powder is obtained which dissolved with the same color in water and dyes polycaprolactam yellow shades.

EXAMPLE 262

10 parts of the dye having the formula:

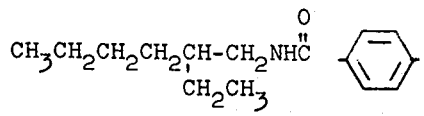
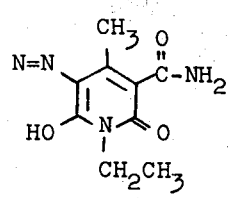

is introduced in portions into 50 parts of 23% oleum while stirring well at 20°C. The mixture is heated to 30°C, stirred for two hours at this temperature and after cooling to 20°C the solution is poured onto 100 parts of crushed ice with efficient stirring. The dye having the formula:

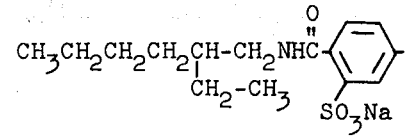
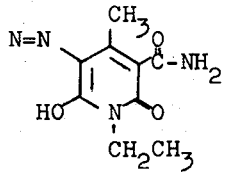

is isolated as usual. It dissolves very well in water and dyes polycaprolactam yellow.

The crystals and the aqueous solution are orange in color.

The dyes set out in the following Table are obtained by a procedure analogous to that described in the Examples and dye polycaprolactam in the shades indicated:

| Example | Dye | Shade of dyeing on polycaprolactam |
|---|---|---|
| 263 | 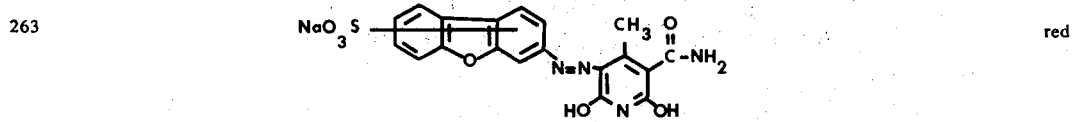 | red |
| 264 | 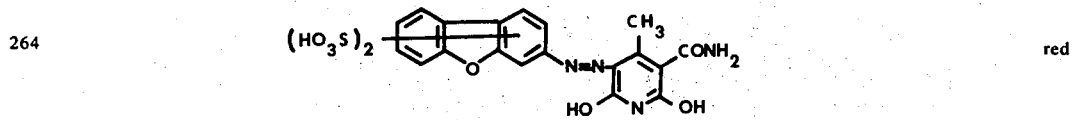 | red |
| 265 | 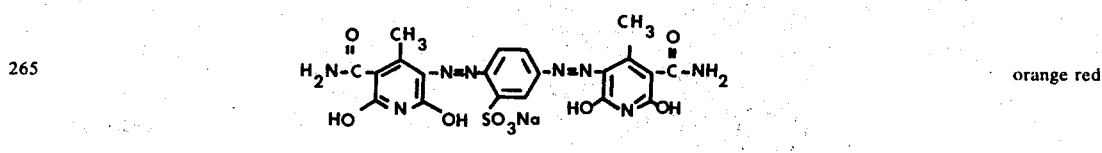 | orange red |
| 266 | 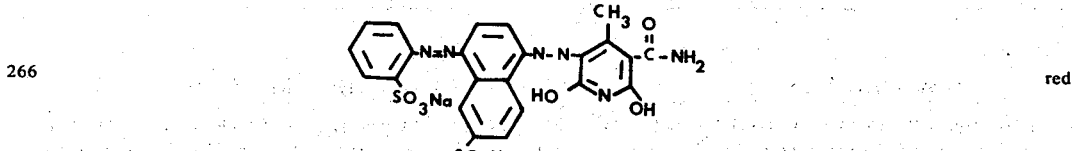 | red |
| 267 | 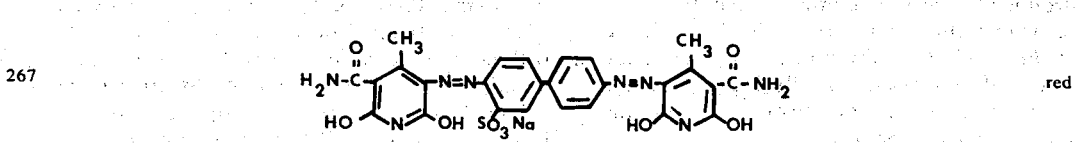 | red |

| Example | Dye | Shade of dyeing on polycaprolactam |
|---------|-----|-----------------------------------|
| 268 | [structure] | |
| 269 | [structure] | |
| 270 | [structure] | red |
| 271 | [structure] | yellow |
| 272 | [structure] | golden yellow |

EXAMPLE 273

0.05 part of the dye of Example 93, 0.3 part of 30% acetic acid and 0.2 part of a commercial leveling agent are dissolved in 400 parts by volume of dye liquor and then 10 parts of a woven or knitted synthetic polyamide cloth is introduced. The temperature of the dye liquor is increased within thirty minutes from 40° to 100°C and kept at this level of sixty minutes. The dyed material is then rinsed and dried. The dyeing obtained is golden, yellow, brilliant, has good fastness to light and good all-round fastness properties.

EXAMPLE 274

7 parts of a woven or knitted woollen fabric is introduced into 420 parts of a dye liquor containing 0.04 part of the dye of Example 213, 0.3 part of 30% acetic acid, 0.5 part of anhydrous ammonium acetate, 1 part of sodium sulfate and 0.1 part of a commercial leveling agent. The temperature of the dye liquor is raised within 45 minutes from 40° to 100°C and held there for 60 minutes. The dyed material is then rinsed and dried.

The dyeing obtained is orange and has good light fastness and all-round fastness properties.

We claim:
1. The compound of the formula
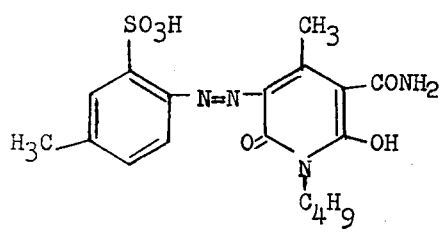
2. The compound of the formula
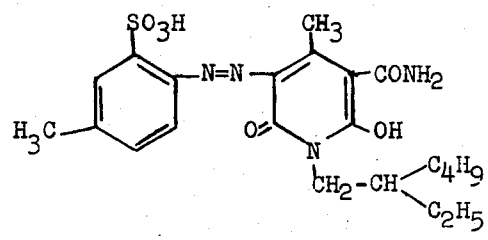
* * * * *